(12) United States Patent
Dunn

(10) Patent No.: US 7,128,927 B1
(45) Date of Patent: Oct. 31, 2006

(54) EMULSIONS FOR IN-SITU DELIVERY SYSTEMS

(75) Inventor: Richard L. Dunn, Fort Collins, CO (US)

(73) Assignee: QLT USA, Inc., Fort Collins, CO (US)

(*) Notice: Subject to any disclaimer, the term of this patent is extended or adjusted under 35 U.S.C. 154(b) by 0 days.

(21) Appl. No.: 09/060,047

(22) Filed: Apr. 14, 1998

(51) Int. Cl.
  A61K 9/107 (2006.01)
  A61K 47/32 (2006.01)
  A61K 47/34 (2006.01)

(52) U.S. Cl. ............. 424/423; 424/484; 424/486; 424/487

(58) Field of Classification Search ......... 424/486–87, 424/484, 423; 514/7, 944, 937
See application file for complete search history.

(56) References Cited

U.S. PATENT DOCUMENTS

| | | |
|---|---|---|
| 2,155,658 A | 4/1939 | Herrmann et al. |
| 3,068,188 A | 12/1962 | Beste et al. |
| 3,218,283 A | 11/1965 | Miller |
| 3,219,527 A | 11/1965 | Gurney |
| 3,328,246 A | 6/1967 | Gottfried et al. |
| 3,463,158 A | 8/1969 | Schmitt et al. |
| 3,520,949 A | 7/1970 | Shepherd et al. |
| 3,696,811 A | 10/1972 | Chen |
| 3,755,558 A | 8/1973 | Schribner |
| 3,760,034 A | 9/1973 | Critchfield et al. |
| 3,767,784 A | 10/1973 | Gluck |
| 3,887,699 A | 6/1975 | Yolles |
| 3,919,773 A | 11/1975 | Freeman |
| 3,931,678 A | 1/1976 | O'Sullivan et al. |
| 3,935,308 A | 1/1976 | Wise et al. |
| 3,939,111 A | 2/1976 | Schollenberger et al. |
| 3,949,073 A | 4/1976 | Daniels et al. |
| 3,975,350 A | 8/1976 | Hudgin et al. |
| 4,148,871 A | 4/1979 | Pitt et al. |
| 4,161,948 A | 7/1979 | Bichon |
| 4,265,247 A | 5/1981 | Lenz et al. |
| 4,294,753 A | 10/1981 | Urist |
| 4,408,023 A | 10/1983 | Gould et al. |
| 4,439,420 A | 3/1984 | Mattei et al. |
| 4,443,430 A | 4/1984 | Mattei et al. |
| 4,447,562 A | 5/1984 | Ivani |
| 4,450,150 A | 5/1984 | Sidman |
| 4,451,452 A | 5/1984 | Deibig et al. |
| 4,455,256 A | 6/1984 | Urist |
| 4,491,479 A | 1/1985 | Lauchenauer |
| 4,526,909 A | 7/1985 | Urist |
| 4,526,938 A | 7/1985 | Churchill et al. |
| 4,563,489 A | 1/1986 | Urist |
| 4,568,536 A | 2/1986 | Kronenthal et al. |
| 4,570,629 A | 2/1986 | Widra |
| 4,582,640 A | 4/1986 | Smestad et al. |
| 4,595,713 A | 6/1986 | St. John |
| 4,596,574 A | 6/1986 | Urist |
| 4,619,989 A | 10/1986 | Urist |
| 4,622,219 A | 11/1986 | Haynes |
| 4,631,188 A | 12/1986 | Stoy et al. |
| 4,650,665 A | 3/1987 | Kronenthal et al. |
| 4,652,441 A * | 3/1987 | Okada et al. |
| 4,663,077 A | 5/1987 | Rei et al. |
| 4,677,139 A | 6/1987 | Feinmann et al. |
| 4,685,883 A | 8/1987 | Jernberg |
| 4,702,917 A | 10/1987 | Schindler |
| 4,715,369 A | 12/1987 | Suzuki et al. |
| 4,721,613 A | 1/1988 | Urquhart et al. |
| 4,745,160 A | 5/1988 | Churchill et al. |
| 4,761,471 A | 8/1988 | Urist |
| 4,767,627 A | 8/1988 | Caldwell et al. |
| 4,767,861 A | 8/1988 | Boulware |
| 4,772,470 A | 9/1988 | Inoue et al. |
| 4,774,227 A | 9/1988 | Piez et al. |
| 4,774,228 A | 9/1988 | Seyedin et al. |
| 4,780,320 A | 10/1988 | Baker |
| 4,789,732 A | 12/1988 | Urist |
| 4,793,336 A | 12/1988 | Wang |
| 4,795,804 A | 1/1989 | Urist |
| 4,800,219 A | 1/1989 | Murdoch et al. |

(Continued)

FOREIGN PATENT DOCUMENTS

CA  1 261 549  9/1989

(Continued)

OTHER PUBLICATIONS

The Merck Index, 11th Ed, S. Budavari Ed., 1989, p. 1514.*

(Continued)

Primary Examiner—Edward J. Webman
(74) Attorney, Agent, or Firm—Schwegman, Lundberg, Woessner & Kluth, P.A.

(57) ABSTRACT

The invention is provides a composition for sustained delivery of a biologically active agent comprising a biologically active mixture and a controlled release formulation. The composition protects the biologically active agent from being destroyed by the controlled release composition. The biologically active mixture includes the biologically active agent and a pharmaceutically acceptable protective carrier. The controlled release formulation includes a pharmaceutically acceptable, biodegradable, matrix forming material that is substantially insoluble in aqueous or body fluids and a pharmaceutically acceptable organic solvent. The biologically active mixture is combined with the controlled release formulation to form an emulsion, the delivery composition, which is then administered to a patient. The protective carrier can be an aqueous substance, a non-aqueous substance or a combination of both. The matrix forming material can be a polymeric material, a non-polymeric material or a combination of both. The organic solvent can have a solubility ranging from a high water solubility to a low water solubility.

11 Claims, No Drawings

U.S. PATENT DOCUMENTS

| | | | |
|---|---|---|---|
| 4,804,691 A | 2/1989 | English et al. |
| 4,818,542 A | 4/1989 | DeLuca et al. |
| 4,857,456 A | 8/1989 | Urist |
| 4,857,602 A | 8/1989 | Casey et al. |
| 4,861,627 A | 8/1989 | Mathiowitz et al. |
| 4,863,472 A | 9/1989 | Törmälä et al. |
| 4,894,373 A | 1/1990 | Young |
| 4,897,268 A | 1/1990 | Tice et al. |
| 4,902,296 A | 2/1990 | Bolander et al. |
| 4,904,478 A | 2/1990 | Walsdorf et al. |
| 4,905,680 A | 3/1990 | Tunc |
| 4,911,931 A | 3/1990 | Baylink |
| 4,912,141 A | 3/1990 | Kronman |
| 4,916,241 A | 4/1990 | Hayward et al. |
| 4,919,939 A | 4/1990 | Baker |
| 4,920,203 A | 4/1990 | Tang et al. |
| 4,921,697 A | 5/1990 | Peterlik et al. |
| 4,932,973 A | 6/1990 | Gendler |
| 4,933,182 A | 6/1990 | Higashi et al. |
| 4,938,763 A | 7/1990 | Dunn et al. |
| 4,939,131 A | 7/1990 | Benedict et al. |
| 4,942,157 A | 7/1990 | Gall et al. |
| 4,946,870 A | 8/1990 | Partain, III et al. |
| 4,954,298 A * | 9/1990 | Yamamoto et al. ......... 264/4.6 |
| 4,961,707 A | 10/1990 | Magnusson et al. |
| 4,962,091 A | 10/1990 | Eppstein et al. |
| 4,981,696 A | 1/1991 | Loomis et al. |
| 4,983,689 A | 1/1991 | Yu |
| 5,007,940 A | 4/1991 | Berg |
| 5,013,553 A | 5/1991 | Southard et al. |
| 5,019,400 A | 5/1991 | Gombotz et al. |
| 5,049,386 A | 9/1991 | Eppstein et al. |
| 5,077,049 A | 12/1991 | Dunn et al. |
| 5,149,543 A | 9/1992 | Cohen et al. |
| 5,176,907 A | 1/1993 | Leong |
| 5,188,837 A | 2/1993 | Domb ......................... 424/450 |
| 5,192,741 A | 3/1993 | Orsolini et al. |
| 5,227,157 A | 7/1993 | McGinity et al. |
| 5,238,714 A | 8/1993 | Wallace et al. |
| 5,250,584 A | 10/1993 | Ikada et al. |
| 5,271,961 A | 12/1993 | Mathiowitz et al. |
| 5,278,201 A | 1/1994 | Dunn et al. |
| 5,278,202 A | 1/1994 | Dunn et al. |
| 5,286,763 A | 2/1994 | Gerhart et al. |
| 5,324,519 A | 6/1994 | Dunn et al. |
| 5,324,520 A | 6/1994 | Dunn et al. |
| 5,326,568 A | 7/1994 | Giampapa |
| 5,340,849 A | 8/1994 | Dunn et al. |
| 5,368,858 A | 11/1994 | Hunziker |
| 5,368,859 A | 11/1994 | Dunn et al. |
| 4,938,763 A | 7/1995 | Dunn et al. |
| 5,599,552 A | 2/1997 | Dunn et al. |
| 5,733,950 A | 3/1998 | Dunn et al. |
| 5,739,176 A | 4/1998 | Dunn et al. |
| 5,744,153 A | 4/1998 | Yewey et al. |
| 5,759,563 A | 6/1998 | Yewey et al. |
| 6,130,200 A * | 10/2000 | Brodbeck et al. |
| 6,294,204 B1 * | 9/2001 | Rossling et al. |
| 6,331,311 B1 * | 12/2001 | Brodbeck et al. |

FOREIGN PATENT DOCUMENTS

| | | |
|---|---|---|
| DE | 29 17 037 | 4/1979 |
| EP | 0 140 766 | 5/1985 |
| EP | 0 159 293 | 10/1985 |
| EP | 0 169 016 | 1/1986 |
| EP | 0 171 173 | 2/1986 |
| EP | 0 241 178 | 10/1987 |
| EP | 0 244 118 | 11/1987 |
| EP | 0 271 831 | 6/1988 |
| EP | 0 297 535 | 1/1989 |
| EP | 0 430 474 | 6/1991 |
| EP | 0442671 | 8/1991 |
| EP | 0 537 559 | 4/1993 |
| EP | 0 539 751 | 5/1993 |
| EP | 0 560 014 | 9/1993 |
| EP | 0 586 838 | 3/1994 |
| EP | 0 649 662 | 4/1995 |
| FR | 2 126 270 | 10/1972 |
| FR | 2 635 685 | 3/1990 |
| GB | 2 017 113 | 10/1979 |
| GB | 2 223 027 | 3/1990 |
| JP | 63-137907 | 6/1988 |
| WO | WO 85/00969 | 3/1985 |
| WO | WO 85/02092 | 5/1985 |
| WO | WO 89/01006 | 2/1989 |
| WO | 95/27481 | 10/1995 |
| WO | 96/21427 | 7/1996 |
| WO | 97/15285 | 5/1997 |
| WO | WO 97/19676 * | 6/1997 |
| WO | 98/27962 | 7/1998 |

OTHER PUBLICATIONS

Budavari, Susan, et al., in *The Merck Index, 12 Edition*, Merck & Co., Inc. Whitehouse Station, NJ,(1996),p. 1636.

Hanks, Patrick, in *The New Oxford Dictionary of English*, Oxford, University Press,(1998),667 and 1288.

Shah, N. H., et al., "A Biodegradable Injectable Implant for Delivering Micro and Macromolecules using Poly (lactic-co-glycolic) Acid (PLGA) Copolymers", *Journal of Controlled Release*, No. 2, Elsevier Science Publishers B.V.,(Mar. 26, 1993), 139-147.

Gref, R. et al., "Biodegradable long—circulating polymeric nanospheres", *Science*, 263:1600-1602 (Mar. 18, 1994).

Holland, S. et al., "Polymers for biodegradable medical devices. 1. The potential of polyesters as controlled macromolecular release systems", *Journal of Controlled Release*, 4:155-180 (1986).

Juni, K. et al., "Control of release rate of bleomycin from polylactic acid microspheres by additives", *Chem. Pharm. Bull.*, 33(4):1609-1614 (1985).

Ouchi, T. et al., "Synthesis and antitumor activity of conjugates of poly($\alpha$-malic acid) and 5-fluorouracils bound via ester, amide or carbamoyl bonds", *Journal of Controlled Release*, 12:143-153 (1990).

Wakiyama, N., et al., "Preparation and evaluation *in vitro* of polylactic acid microspheres containing local anesthetics", *Chem. Pharm. Bull.*, 29(11):3363-3368 (1981).

Zilch, H., et al., "The sustained release of cefotaxim from a fibrin-cefotaxim compound in treatment of osteitis", *Arch. Orthop. Trauma Surg.* 106:36-41 (1986).

*Encyclopedia of Polymer Science and Engineering*, John Wiley & Sons Inc., 2:236-237 (1985).

Billmeyer, F., *Textbook of Polymer Science*, 3rd Ed., John Wiley & Sons, pp. 390-391 (1984).

*Biocompatibility of Clinical Implant Materials* (Ch. 9: "Biodegradable Polymers", by D. K. Gilding), pp. 209-232 (date unknown).

*Hawley's Condensed Chemical Dictionary*, 11th Ed. (1987), Van Nostrand Reinhold Company, New York; pp. 145-146, 932-933, 944-945.

* cited by examiner

EMULSIONS FOR IN-SITU DELIVERY SYSTEMS

BACKGROUND OF THE INVENTION

A variety of approaches have been developed for administering a biologically active agent to a patient in a continuous or sustained manner. However, currently available approaches suffer from one or more disadvantages or limitations.

In many conventional controlled release systems, the active agents are incorporated into solid, monolithic polymeric matrices. The matrices are surgically implanted into patients' bodies and control the release of active agents into the patients' systems. Often, however, the sizes and shapes of the matrices and the surgical implantation lead to patient discomfort and complications. In recent years, microstructures, such as lipospheres, liposomes, microcapsules, microparticles, and nanoparticles have been developed to overcome these problems. The microstructures contain the active agents and are introduced into a patients' bodies as dispersions. However, when inserted into a body cavity where there is considerable fluid flow, such as the mouth or eye, microstructures may be poorly retained due to their small size and discontinuous nature. Microstructure systems also lack reversibility. If complications arise after introduction, it is difficult to remove the microstructures without extensive and complex surgical intervention.

Other controlled release delivery systems are flowable composition that can be administered using a syringe. Upon contact with body fluids, the delivery system is transformed in situ to form a solid implant. Exemplary flowable polymeric compositions are described in U.S. Pat. Nos. 4,938,763; 5,278,201; and 5,278,202. As the delivery system forms a solid matrix, the active agent is trapped or encapsulated within the matrix. The release of the active agent then follows the general rules for the dissolution or diffusion of a drug from within a polymeric matrix.

Irrespective of their physical character as monolithic matrices, microstructures or flowable compositions, these delivery systems can not be effectively used with all biologically active agents. Some biologically active agents may be destroyed or dissolved by the polymeric formulations and carriers used in these systems. For example, peptides or proteins may be denatured by the solvents used to dissolve the polymers. RNA or DNA compounds and antigens may be affected. Cellular treatments are also difficult to administer using known sustained release systems. The sustained release formulations often provide an environment that is too harsh for cellular survival and therefore causes destruction or death of the cells. Therefore, an improved method for sustained release of a biologically active agent in which the active agent is protected from the sustained release formulation would be desirable.

SUMMARY OF THE INVENTION

The invention is directed to a composition for sustained delivery of a biologically active agent comprising a biologically active mixture and a controlled release formulation. The composition protects the biologically active agent from being destroyed by the components of the sustained release system.

The biologically active mixture includes the biologically active agent and a pharmaceutically acceptable protective carrier. The controlled release formulation includes a pharmaceutically acceptable, biodegradable matrix forming material that is substantially insoluble in aqueous media and a pharmaceutically acceptable organic solvent.

According to the invention, the biologically active mixture containing the biologically active agent and the protective carrier is combined with the controlled release formulation, to form an emulsion, suspension or dispersion (the delivery composition), just prior to administration to a patient. In the delivery composition, the biologically active agent remains suspended or dissolved in the protective carrier and is therefore isolated from the components of the controlled release formulation.

The protective carrier can be an aqueous substance, non-aqueous substance or a combination of both. The matrix forming material can be a polymeric material, a non-polymeric material or a combination of both. Preferably, the matrix forming material is biodegradable. The organic solvent can have either a high water solubility or a low water solubility.

DETAILED DESCRIPTION OF THE INVENTION

The invention provides a composition and method for controlled release delivery of a biologically active agent wherein the initial burst of biologically active agent released into a patient is reduced and wherein the biologically active agent is protected from the polymeric formulation. The delivery composition is administered as a "flowable" material. "Flowable" means having a viscosity that will permit displacement of the flowable material with or without application of pressure. A flowable delivery composition is manipulatable, is displaceable through a small to moderate sized orifice and may be shaped and molded within the tissue defect. Flowable compositions in this context include those having a consistency from that of an emulsion or suspension with a low viscosity or water-like consistency, to that of a high viscosity putty or paste. Advantageously, the flowability of the delivery composition allows it to conform to irregularities, crevices, cracks, and/or holes in the tissue defect.

Generally, the delivery composition of the invention consists of two components: a biologically active mixture and a controlled release composition. The biologically active mixture, the controlled release component and resulting solid implant are "biocompatible" in that they do not cause substantial tissue irritation or necrosis at the implant site. "Biodegradable" means that the resulting implant degrades over time by the action of enzymes, hydrolytic action and/or other similar mechanisms. "Bioerodible" means that the implant erodes or degrades over time due, at least in part, to contact with substances found in the surrounding tissue fluids, or by cellular action. "Bioabsorbable" means that the resulting implant is broken down and absorbed within the patient's body, for example, by a cell or tissue. "Implant site" means a site, in or on which the controlled release formulation is formed or applied, for example, a soft tissue such as muscle or fat, or a hard tissue such as bone. Examples of other implant sites include, but are not limited to, a tissue defect such as a tissue regeneration site; a void space such as a periodontal pocket, a surgical incision or other formed pocket or cavity; a natural cavity such as the oral, vaginal, rectal or nasal cavities, and the cul-de-sac of the eye.

Delivery Composition

The delivery composition of the invention provides a system for sustained, continuous delivery of drugs, medicaments and other biologically-active agents to tissues adjacent or distant from the site of administration. Generally, the delivery composition consists of an emulsion, suspension or dispersion of two components: a biologically active mixture and a controlled release composition. The biologically active mixture includes a biologically active agent and a pharmaceutically acceptable protective carrier. The controlled release composition includes a pharmaceutically acceptable organic solvent and a pharmaceutically acceptable, biodegradable matrix forming material that is substantially insoluble in aqueous media.

The biologically active mixture is combined with the controlled release composition to form the delivery composition just prior to administering the delivery composition to a patient. It is important that the biologically active mixture is combined with the controlled release component close to the time of administration, such that the delivery composition remains an emulsion or dispersion during its administration. The interval between the formation of the delivery composition and its administration will depend upon the physical and chemical stability of the emulsion or dispersion. In general, an interval of up to 7 days can be used, preferably up to 1 day, more preferably up to 10 hours, most preferably up to 1 hour.

When the controlled release formulation contacts an aqueous medium, such as water or body fluids, the organic solvent disperses into the surrounding body fluids and the matrix forming material coagulates or precipitates to form a solid implant in which the biologically active mixture is entrapped. The biologically active agent within the mixture is gradually released from the solid implant by diffusion, dissolution and/or biodegradation of the implant matrix.

Biologically Active Mixture

According to the invention, a biologically active agent is combined with a carrier to form a biologically active mixture. As used herein, a biologically active agent is an agent that is capable of providing a local or systemic biological, physiological or therapeutic effect in the body of a patient. The biologically active agent is combined with the carrier to form a mixture, ranging in physical form from a solution to an emulsion. The solution involves a uniform distribution of the components. The emulsion involves a stable mixture of two or more immiscible liquids which form a suspension or dispersion having a continuous phase and a dispersed phase.

The delivery composition includes the biologically-active agent in an amount effective to provide the desired level of biological, physiological, pharmacological and/or therapeutic effect in the patient. There is generally no critical upper limit on the amount of the biologically active agent that can be included in the composition. For optimal performance, the concentration of the bioactive agent should not be so high that the controlled release composition cannot effectively control the rate of release of the bioactive agent. The lower limit of the amount of bioactive agent incorporated into the delivery composition depends on the activity of the bioactive material and the period of time desired for treatment. Generally, one skilled in the art of formulations can determine the appropriate amount of biologically active agent to incorporate into the delivery composition as a function of the patient's condition, the physical characteristics of the biologically active agent and the prescribed treatment regimen for the malcondition of the patient.

Biologically Active Agents

Examples of suitable biologically active agents include substances capable of preventing an infection systemically in the animal or locally at the defect site, for example, anti-inflammatory agents such as hydrocortisone, and prednisone; antibacterial agents such as penicillin, cephalosporins, bacitracin, tetracycline, doxycycline, gentamycin, quinolines, neomycin, clindamycin, kanamycin, azithromycin and metronidazole; antiparasitic agent such as quinacrine, chloroquine, and vidarbine; antifungal agents such as nystatin; antiviral agent such as acyclovir, ribarivin, and interferons; analgesic agents such as salicylic acid, acetaminophen, ibuprofen, naproxen, piroxicam, flurbiprofen, and morphine; local anesthetics such as cocaine, lidocaine, bupivacaine and benzocaine; immunogens (vaccines) for simulating antibodies against hepatitis, influenza, measles, rubella, tetanus, polio, and rabies; peptides such as leuprolide acetate (an LH-RH agonist), nafarelin, and ganirelix.

Substances, or metabolic precursors thereof, which are capable of promoting growth and survival of cells and tissues or augmenting the functioning of cells can also be used, for example, a nerve growth promoting substance, such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-α), transforming growth factor-β, (TGF-β), epidermal growth factor (EGF), fibroblast growth factor (FGF), and interleukin-1 (IL-1); an osteoinductive agent or bone growth promoting substance such a bone chips or demineralized bone material; and antineoplastic agents such as methotrexate, 5-fluorouracil, adriamycin, vinblastine, cisplatin, paclitaxel, floxuridine, tumor-specific antibodies conjugated to toxins, and tumor necrosis factor.

Other suitable biologically active agents include hormones such as progesterone, testosterone, follicle simulating hormone (FSH) (used for birth control and fertility-enhancement), insulin, and somatotropins; antihistamines such as diphenhydramine and chlorphencramine; cardiovascular agents such as digitalis, nitroglycerin, papaverine and streptokinase; anti-ulcer agents such as cimetidine hydrochloride, and isopropamide iodide; bronchodilators such as metaproternal sulfate and aminophylline; vasodilators such as theophylline, niacin and minoxidil; central nervous system agents such as tranquilizer, b-adrenergic blocking agents, and dopamine; antipsychotic agents such as risperidone and olanzapine; narcotic antagonists such as naltrexone, naloxone and buprenorphine.

Additionally, the delivery composition of the invention can be used to deliver genes which encode biologically useful proteins, such as growth hormone, growth hormone releasing factor, pituitary factors, adrenal factors, pancreatic factors, interferon factors, prostaglandin releasing factors and the like. The deliver composition of the invention can also be used to deliver cells, for example, cells such as fibroblasts, osteoblasts, chondrocytes, retinal pigmented epithelia, epithelia, β-islet cells, mesenchymal stem cells, and other cells within the body. In addition, the delivery composition can be used to delivery microparticles or nanoparticles which would normally be dissolved or destroyed by the organic solvents of the delivery system. These microparticles or nanoparticles can contain biologically active agents themselves which are desirable for delivery within the body.

For more examples of suitable biologically active agents, see U.S. Pat. No. 5,234,529, the disclosure of which is incorporated by reference herein.

Carrier

According to the invention, the biologically active agent is combined with a protective carrier to form a biologically active mixture. The biologically active agent is suspended or entrained within the protective carrier, and is isolated from the controlled release component of the delivery composition. The protective carrier insulates and protects the biologically active agent from being dissolved or destroyed by the controlled release composition. Additionally, because the protective carrier isolates the biologically active agent from the organic solvent of the delivery composition, the biologically active agent is less likely to disperse into the surrounding aqueous medium along with the organic solvent. Instead, the biologically active agent is constrained within the delivery composition as it solidifies to form a solid implant. Consequently, the initial burst of biologically active agent released into a patient's system may be reduced.

According to the invention, the protective carrier can be an aqueous or non-aqueous substance as long as the protective carrier is capable of forming a mixture with the biologically active agent so that the biologically active agent either is dissolved in the carrier to form a solution or is suspended in the carrier to form an emulsion or dispersion. In some instances it may be more preferable to use a non-aqueous carrier, for example, with highly water soluble drugs such as doxycycline, 5-fluorouracil, and ibuprofen. In other applications, it may be preferable to use an aqueous carrier, for example, with peptides, proteins or cells which may be affected by non-aqueous carriers.

Suitable non-aqueous carriers include pharmaceutically acceptable oils, low melting waxes, fats, lipids, liposomes and any other pharmaceutically acceptable substance that is lipophilic, substantially insoluble in water body, fluid, and is biodegradable and/or eliminatable by natural processes of a patient's body. Oils of plants such as vegetables and seeds are included. Examples include oils made from corn, sesame, cannoli, soybean, castor, peanut, olive, arachis, maize, almond, flax, safflower, sunflower, rape, coconut, palm, babassu, and cottonseed oil; waxes such as carnoba wax, beeswax, and tallow; fats such as triglycerides, lipids such as fatty acids and esters, and liposomes such as red cell ghosts and phospholipid layers.

Examples of suitable aqueous carriers include pharmaceutically acceptable compositions such as water, saline, physiological buffer solutions and cell-culture media such as agar, bovine medium, Ficoll medium and any other aqueous based medium optionally containing pharmaceutically acceptable nutrients, minerals, amino acids, lipids, buffers, vitamins and the like.

Additional Components

The biologically active mixture can also include other components such as emulsifying agents, surfactants, excipients, colorants and the like to stabilize the emulsions or protect the biologically active agents.

Controlled Release Formulation

The delivery composition of the invention also includes a controlled release formulation which includes a matrix forming material and a solvent.

Matrix Forming Material

According to the invention, the controlled delivery system includes a matrix forming material. The matrix forming material can be made from a biocompatible polymer, copolymer or nonpolymeric material, or a combination of polymeric and nonpolymeric material, that is substantially insoluble in aqueous fluids, such as water or body fluids, and biodegradable and/or bioerodible within the body of an animal. As used herein, "substantially insoluble" means that the matrix forming material Does not dissolve in an aqueous medium. The matrix forming material is capable of Being at least partially solubilized in an organic solvent. As used herein, "at least partially solubilized" means that the matrix forming material dissolves at a concentration from about 10% to about 70% by weight in the organic solvent.

Upon contacting an aqueous environment, such as a patient's body fluids, the organic solvent of the controlled delivery composition dissipates or disperses into the surrounding aqueous fluids and the matrix forming material coagulates or precipitates to form a solid implant. When the controlled delivery composition is administered in combination with a biologically active mixture, such as that described above, the biologically active agent is entrained in the solid implant. As the matrix of the implant degrades over time, the biologically-active agent is released into adjacent tissue fluids at a controlled rate. The rate at which the biologically-active agent is released from the matrix may be varied, for example, by the solubility of the biologically-active agent in an aqueous medium, the distribution of the agent within the matrix, and the size, shape, porosity, solubility and biodegradability of the matrix.

The concentration of matrix forming material in the organic solvent can vary depending on the desired viscosity of the delivery composition. In applications where the delivery composition is injected with standard syringes and needles, the viscosity has to be low enough to allow the material to be easily injected. In other applications such as putties or pastes, the viscosity may be much higher. Because the non-polymeric materials tend to have relatively low molecular weights, they form solutions with low viscosities which can be easily injected through standard syringes and needles.

Typically, the concentration of matrix forming material ranges from about 0.1 grams per ml of solvent to about 3 grams per ml of solvent, preferably from about 0.5 grams to about 2 grams per ml.

Polymeric Materials

Suitable polymeric materials include polymers or copolymers, such as thermoplastic polymers that are biocompatible, biodegradable, bioerodible and/or bioabsorbable and are substantially insoluble in aqueous fluids. Examples of suitable thermoplastic polymers are those having formulas incorporating monomeric units including lactides, glycolides, caprolactones, anhydrides, amides, urethanes, esteramides, orthoesters, dioxanones, acetals, ketals, carbonates, phosphazenes, hydroxybutyrates, hydroxyvalerates, alkylene oxalates, alkylene succinates, and amino acids. The formulas may incorporate a single monomeric unit or may be copolymers or terpolymers of two or more of these foregoing monomeric units, with the monomeric order being random or block. Physical combinations or mixtures these polymers, copolymers and terpolymers may also be employed. Polymers of lactide, caprolactone, glycolide and hydroxybutryate and copolymers of the monomeric units of these preferred monomeric units are preferred.

Nonpolymeric Materials

Suitable non-polymeric materials include sterols, such as cholesterol, stigmasterol, β-sitosterol, and estradiol; cholesteryl esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di-, and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monglycerides.

Organic Solvents

The matrix forming material is combined with a suitable organic solvent to form the controlled release formulation. Upon contact with an aqueous medium, such as water or body fluids, the organic solvent diffuses or leaches into the surrounding aqueous medium and the matrix forming material, which is substantially insoluble in aqueous fluids, precipitates or coagulates to form a solid implant.

Suitable solvents for use in the present polymer formulation are those which are biocompatible, pharmaceutically-acceptable, and will at least partially dissolve the polymeric or non-polymeric material. According to the invention, the solvent has a solubility in aqueous medium, ranging from miscible to dispersible and is capable of diffusing into an aqueous medium, for example, tissue fluids, such as blood serum, lymph, cerebral spinal fluid (CSF), and saliva. In addition, the solvent is preferably biocompatible.

The solubility or miscibility of the matrix forming material in a particular solvent may vary according to factors such as crystallinity, hydrophilicity, capacity for hydrogen bonding, and molecular weight. Consequently, the molecular weight and concentration of the matrix forming material can be adjusted to modify the solubility of the matrix forming material in the controlled release formulation. Preferably, the matrix forming material has a low degree of crystallization, a low degree of hydrogen bonding, low solubility in water and high solubility in organic solvents.

The organic solvent can have water solubility ranging from a high water solubility i.e., from those forming a 20% by weight solution in water to those completely miscible in all properties, to a low water solubility i.e., those forming solution with less than 20% by weight of the solution in water. An organic solvent with a "high" water solubility rapidly diffuses or dissipates from the delivery composition into the surrounding aqueous fluids. Thus, the matrix forming material rapidly precipitates or coagulates to form a solid implant. As used herein, "rapidly" means that the solid implant takes about 1 to about 120 minutes to form, more preferably, about 1 to about 30 minutes. Typically, a "high" water solubility organic solvent has a water solubility from about 20% to about 90% weight percent.

In contrast, an organic solvent having a "low" solubility in an aqueous medium will dissipate slowly in the aqueous medium. Thus, the matrix forming material slowly precipitates or coagulates to form a solid implant. As used herein, "slowly" means that the solid implant takes about 5 hours to about 30 hours to form, more preferably takes about 5 hours to about 10 hours to form. Typically, a "low" water soluble organic solvent has a water solubility of about 2% to about 20% weight percent.

High Water Solubility Solvents

A high water solubility solvent can be used in the controlled release composition. Preferably, a high water solubility solvent is used when a short solidification time for the controlled release system is needed in order to form a solid implant that maintains its shape and stays in place.

Useful high water solubility organic solvents include, for example, substituted heterocyclic compounds such as N-methyl-2-pyrrolidone (NMP) and 2-pyrrolidone; $C_2$ to $C_{10}$ alkanoic acids such as acetic acid, lactic acid and heptanoic acid; esters of hydroxy acids such as methyl lactate, ethyl lactate, alkyl citrate and the like; monoesters of polycarboxylic acids such as monomethyl succinate acid, monomethyl citric acid and the like, ether alcohols such as 2-ethoxyethanol, ethylene glycol dimethyl ether, glycofurol and glycerol formal; alcohols such as ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol; solketal; dialkylamides such as dimethylformamide, dimethylacetamide; dimethylsulfoxide (DMSO) and dimethylsulfone; lactones such as ε-caprolactone and butyrolactone; cyclic alkyl amides such as caprolactam; aromatic amides such as N,N-dimethyl-m-toluamide, and 1-dodecylazacycloheptan-2-one; and mixtures and combinations thereof. Preferred solvents include N-methyl-2-pyrrolidone, 2-pyrrolidone, dimethylsulfoxide, ethyl lactate, glycofurol, glycerol formal, and isopropylidene glycol.

Low Water Solubility Solvents

A low water solubility solvent may also be used in the controlled release composition. Preferably, a low water solubility solvent is used when it is desirable to have a slow coagulation rate for the solid implant, for example, in applications where the implant does not need to maintain its shape and it is desirable that the controlled release composition flow to more easily fit the tissue site and prevent tissue damage, such as in an intramuscular injection.

Examples of low water soluble solvents include esters of carbonic acid and alkyl alcohols such as propylene carbonate, ethylene carbonate and dimethyl carbonate alkyl esters of mono-, di-, and tricarboxylic acids, such as 2-ethyoxyethyl acetate, ethyl acetate, methyl acetate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as methyl ethyl ketone, tetrahydrofuran as well as other carbonyl, ether, carboxylic ester, amide and hydroxy containing liquid organic compounds having some solubility in water. Propylene carbonate, ethyl acetate, triethyl citrate, isopropyl myristate, and glyceryl triacetate are preferred because of biocompatitibility and pharmaceutical acceptance.

Additionally, mixtures of the foregoing high and low water solubility solvents providing varying degrees of solubility for the matrix forming material can be used to alter the coagulation rate of the matrix forming material. Examples include a combination of N-methylpyrrolidone and propylene carbonate, which provides a more hydrophobic solvent than N-methylpyrrolidone alone, and a combination of N-methyl pyrrolidone and polyethylene glycol, which provides a more hydrophilic solvent than N-methylpyrrolidone alone.

Additives for the Delivery Composition

Surfactants and/or emulsifying agents such as sodium dodecylsulfonate or polyvinyl alcohol can be added to the delivery composition to improve or stabilize the emulsion. A "stable" emulsion, is one which the components do not separate from the emulsion in a short time such as 1–24 hours. The literature on microencapsulation with biodegradable polymers provides appropriate materials and conditions for emulsions.

Other additives include release rate modification agents, such as those discussed in U.S. Pat. No. 5,702,716 which issued from application Ser. No. 07/7767,816, filed Oct. 15, 1991, the disclosures of which are incorporated by reference herein.

Formation of the Delivery Composition

The delivery composition of the invention is an emulsion or dispersion of the biologically active mixture in the controlled release formulation. While the term "emulsion" is typically used in connection with two immiscible liquids, in the context of this invention it is also used in connection with a liquid and a paste, putty or semisolid. The terms "suspension" and "dispersion" in their ordinary, usual meaning also describe this delivery composition.

To prepare the delivery composition of the invention, any known technique for suspending, dispersing or emulsifying one material within another can be used. For the present invention such techniques involve combination of the biologically active mixture and the controlled release formulation and either simultaneously or subsequently agitating, shaking, stirring, whipping, agitating, frothing, bubbling or otherwise manipulating to form small particles, droplets or micelles of the biologically active material within the controlled release formulation. Additionally, the biologically active material may be sprayed, aerosolized, or otherwise converted or comminuted into small droplets or particles which are then combined with the controlled release formulation.

In a typical preparation, an appropriately sized syringe containing the flowable biologically active mixture is connected to an appropriately sized syringe half filled with a flowable controlled release formulation. The plunger of the syringe containing the mixture is actuated to transport the mixture into the formulation syringe. The plungers of the two syringes are reciprocated a number of times to agitate the mixture and formulation and convert the mixture into small droplets suspended within the formulation. The prepared flowable delivery composition is ready for injection and implant formation.

Formation of a Solid Implant

In general, a solid implant is formed by administering the flowable delivery composition into a target tissue or onto the surface of such tissue. The administration can be accomplished by any convenient technique. For example, the formulation can be applied by brushing, spraying, extruding, dripping, injecting, or painting. Alternately, a delivery composition having a high viscosity, such as that of a putty or paste, can be administered by forming an incision, placing the delivery composition at the implant site and closing the incision, for example, by suturing.

Optionally, after the delivery composition is administered to the implant site, an aqueous solution, such as a saline solution, can be applied over the delivery composition to cause matrix formation. This option especially can be used in situations where the tissue itself does not contain sufficient body fluid to cause matrix formation, e.g., such as in a bone defect.

Use of the Delivery Composition

The delivery composition can be used to administer a biologically active agent to a patient in a sustained manner. The delivery composition of the invention enables the a biologically active agent to be delivered in a sustained manner while protecting the biologically active agent from dissolution or degradation by the controlled release composition.

Providing a Sustained Release

In a first embodiment, the delivery composition of the invention can be used to provide a sustained release of a biologically active agent. To prepare a composition which will have a sustained release effect when administered to a patient, a biologically active agent is combined with a protective carrier to form a biologically active mixture. The biologically active mixture is then combined with a controlled release composition and agitated to form the delivery composition.

The delivery composition can be injected into a patient's body using a standard syringe and needle, such as a 1 cc syringe and a 22 gauge needle. When the delivery composition is administered to a patient, the organic solvent dissipates into the surrounding body fluids. As the solvent dissipates, the matrix forming material precipitates or coagulates to form a solid implant. Because the biologically active agent is entrained in the carrier and is isolated from the organic solvent, it does not dissipate into the surrounding aqueous fluids with the organic solvent. Instead, the biologically active agent suspended in the carrier remains with the matrix forming material as it coagulates. Once the solid implant is formed, droplets of the biologically active agent suspended in the protective carrier are entrained within the matrix. Depending upon its water solubility, the protective carrier may quickly, slowly or indiscernibly dissipate from the matrix, but notwithstanding the presence or absence of the protective carrier, the biologically active agent will be released over time from the matrix or the matrix and carrier.

If the protective carrier is immiscible with the controlled release composition and is immiscible to slightly soluble in water, it is preferably used to provide protection of the biologically active agent which is then combined with a controlled release composition. Because the biologically active agent is dissolved or suspended in the water immiscible or slightly soluble protective carrier, it is isolated from the organic solvent and matrix forming material of the controlled release composition and the protective carrier remains with the implant at least substantially throughout the life of the implant. This arrangement provides optimal protection of the biologically active agent against dissolution or degradation by the organic solvent or matrix forming material although other arrangements using differing protective agents having up to moderate solubility in water can also be used. This embodiment is particularly useful when the biologically active agent is particularly susceptible to dissolution or degradation, such as a protein, a gene, a polymeric nanoparticle or a cell.

The foregoing disclosure teaches to those of skill in the art the aspects of the invention including how to make and use the invention. The following examples are meant to provide further elucidation of the invention but are not meant as limitations thereof.

EXAMPLES

Example 1

Use of Water in Polymer Solutions Prepared with Low Water-Soluble Solvents (Water-in-Oil Emulsion)

Poly (DL-lactide-co-glycolide) with an inherent viscosity of 0.2 dL/g and containing carboxyl end groups (PLGH) was dissolved in propylene carbonate (PC) to form a solution with 40% by weight polymer. The polymer solution was then added to a polypropylene syringe with a male luer-lok fitting. Water was added to a second polypropylene syringe with a female luer-lok fitting, and the two syringes were coupled together and the contents mixed back and forth between the two syringes for about 25 cycles to form an emulsion. The emulsion was withdrawn into the syringe with the male luer-lok fitting, the two syringes disconnected, and a 20-gauge cannula attached to the male luer-lok fitting. The emulsion was then expressed into 5 mL of phosphate buffered solution (PBS) in a glass vial where it coagulated to form a soft gelatinous, but intact implant.

| PLGH/PC Solution (mL) | Water (mL) | Emulsion | Implant |
| --- | --- | --- | --- |
| 0.5 | 0.5 | Good | Soft, Intact |
| 1.0 | 0.5 | Better | Soft, Intact |

If a solvent sensitive biologically active agent such as a peptide, protein, or DNA or cell were dissolved or dispersed within the aqueous phase, it would be protected from the organic solvent and polymer.

Example 2

Use of Water in Polymer Solutions Prepared with Highly Water-Soluble Solvent

PLGH with an inherent viscosity of 0.2 dL/g was dissolved in N-methyl-2-pyrolidone (NMP) to give a solution with 40% by weight polymer. This polymer solution (0.5 mL) was placed in a polypropylene syringe and mixed with water (0.5 mL) in a separate syringe as described in Example 1. Upon mixing, the polymer solution immediately coagulated with the syringes to form a solid polymer plug, which could be removed only with great difficulty from the syringes.

Example 3

Use of Oils in Polymer Solutions Prepared with Low Water-Soluble Solvents (Oil-in-Oil Emulsion)

PLGH with an inherent viscosity of 0.2 dL/g was dissolved in PC to form a solution with 40% by weight polymer. The polymer solution was loaded into a polypropylene syringe and mixed with either sesame oil (SO), peanut oil (PO), or castor oil (CO; polyoxy 35; Incrosas 35 NF; Croda Inc.), in another syringe as described in Example 1. The emulsion that formed was then injected into 5 mL of water in a glass vial to form a soft gelatinous, but intact implant.

| PLGH/PC Solution (mL) | SO (mL) | PO (mL) | CO (mL) | Emulsion | Implant |
| --- | --- | --- | --- | --- | --- |
| 0.5 | 0.5 | | | Good | Soft, Intact |
| 1.0 | 0.5 | | | Good | Soft, Intact |
| 0.5 | | 0.5 | | Good | Soft, Intact |
| 1.0 | | 0.5 | | Good | Soft, Intact |
| 0.5 | | | 0.5 | Fair | Soft, Intact |
| 1.0 | | | 0.5 | Good | Soft, Intact |

Example 4

Use of Oils in Hydrophilic Polymer Solution Prepared with a Highly Water-Soluble Solvent (Oil-in-Oil Emulsion)

PLGH was dissolved in NMP to form a solution with 40% by weight polymer. The polymer solution was loaded into a polypropylene syringe and mixed with either SO, PO or CO in another syringe as described in Example 1. The emulsion that formed was then injected into 5 mL of water in a glass vial.

| PLGH/NMP Solution (mL) | SO (mL) | PO (mL) | CO (mL) | Emulsion | Implant |
| --- | --- | --- | --- | --- | --- |
| 0.5 | 0.5 | | | Poor | Transparent Gel |
| 1.0 | 0.5 | | | Poor | Transparent Gel |
| 0.5 | | 0.5 | | Fair | Transparent Gel |
| 1.0 | | 0.5 | | Fair | Transparent Gel |
| 0.5 | | | 0.5 | Good | Soft, Intact |
| 1.0 | | | 0.5 | Good | Soft, Intact |

Example 5

Use of Oils in Hydrophobic Polymer Solution Prepared with a Highly Water-Soluble Solvent (Oil-in-Oil Emulsion)

Poly(DL-lactide)(PLA) with an inherent viscosity of 0.37 dL/g was dissolved in NMP to give a polymer solution with 37% by weight polymer. The polymer solution was then loaded into a polypropylene syringe and mixed with either sesame oil (SO), peanut oil (PO) or castor oil (CO) in another syringe, as described in Example 1. The emulsion was then injected into 5 mL of water in a glass vial to form a soft, intact implant.

| PLA/NMP Solution (mL) | SO (mL) | PO (mL) | CO (mL) | Emulsion | Implant |
| --- | --- | --- | --- | --- | --- |
| 0.5 | 0.5 | | | Poor | Soft, gelatinous |
| 1.0 | 0.5 | | | Good | Soft, gelatinous |
| 0.5 | | 0.5 | | Poor | Soft, gelatinous |
| 1.0 | | 0.5 | | Good | Soft, gelatinous |
| 0.5 | | | 0.5 | Good | Soft, Intact |
| 1.0 | | | 0.5 | Good | Soft, Intact |

Example 6

Use of a Water-in-Oil Emulsion in Polymer Solutions Prepared with a Low Water-Soluble Solvent (Water-in-Oil-in-Oil Emulsion)

Water (0.25 mL) in one polypropylene syringe was mixed with 0.25 mL of either sesame oil (SO), peanut oil (PO), castor oil (CO) in another syringe to form a water-in-oil emulsion. This emulsion was then drawn into one syringe, the two syringes uncoupled, and the syringe containing the water-in-oil emulsion was connected to another polypropylene syringe containing a solution of PLGH (inherent viscosity of 0.20 dL/g) in propylene carbonate (PC). The water-in-oil emulsion and the polymer solution were then mixed as described in Example 1 to form a water-in-oil-in-oil emulsion. This emulsion was then injected into 5 mL of water in a glass vial.

| PLGH/PC Solution (mL) | Water (mL) | SO (mL) | PO (mL) | CO (mL) | Emulsion | Implant |
|---|---|---|---|---|---|---|
| 0.5 | 0.25 | 0.25 | | | Good | Soft, Intact |
| 1.0 | 0.25 | 0.25 | | | Good | Soft, Intact |
| 0.5 | 0.25 | | 0.25 | | Good | Soft, Intact |
| 1.0 | 0.25 | | 0.25 | | Good | Soft, Intact |
| 0.5 | 0.25 | | | 0.25 | Good | Gelatinous |
| 1.0 | 0.25 | | | 0.25 | Good | Gelatinous |

What is claimed is:

1. A composition for delivering a biologically active agent, comprising: an emulsion of a biologically active mixture and a controlled release formulation, the biologically active mixture consisting essentially of the biologically active agent and a pharmaceutically acceptable, aqueous medium as a protective carrier; and the controlled release formulation comprising a pharmaceutically acceptable, biodegradable thermoplastic polymer that is substantially insoluble in an aqueous or body fluid and a pharmaceutically acceptable organic solvent having a water solubility of from about 2 percent to about 20 percent by weight relative to a weight of a combination of organic solvent and water, and wherein the concentration of polymer in organic solvent ranges from about 0.5 gm per ml to about 3 gm per ml, the volume to volume ratio of the controlled release formulation to the biologically active mixture is about 1:1 to about 2:1, and the composition forms a solid implant in which the biologically active mixture is entrapped when the controlled release formulation contacts an aqueous medium or body fluid.

2. A precomposition suitable for preparing a composition according to claim 1, comprising separate containers of the biologically active mixture and controlled release formulation, which containers are adapted to cause combination of the biologically active mixture and controlled release formulation.

3. A composition of claim 1, wherein the biologically active agent is selected from the group consisting of an antiinflammatory agent, an antibacterial agent, an antifungal agent, an analgesic agent, an anesthetic agent, an immunogen, a vaccine, an antineoplastic agent, a growth or survival agent, a hormone, a cardiovascular agent, an anti-ulcer agent, a bronchial agent, a central nervous system agent, a gene, a gene fragment, an insertion vector carrying a gene or gene fragment, and any combination or multiple thereof.

4. A composition of claim 1 wherein the thermoplastic polymer formula contains monomeric units selected from the group consisting of lactide, glycolide, caprolactone, anhydride, amide, urethane, esteramide, orthoester, dioxanone, acetal, ketal carbonate, phosphazene, hydroxybutyrate, hydroxyvalerate, alkylene oxalate, alkylene succinate, amino acid and any copolymer and terpolymer combination of these monomeric units in random order or in block order.

5. A composition of claim 4 wherein the monomeric units include lactide, glycolide, caprolactone, hydroxybutyrate, and any combination thereof.

6. A composition of claim 1, wherein the emulsion is a water-in-oil emulsion.

7. A composition of claim 1 wherein the thermoplastic polymer is in mixture with a pharmaceutically acceptable, biodegradable non-polymeric material that is substantially insoluble in aqueous or body fluid and is a solid at body temperature.

8. A composition of claim 1 wherein the aqueous carrier has a water-like consistency and is water, saline, physiological buffer solution, cell-culture medium, aqueous nutrient medium, aqueous mineral medium, aqueous amino acid medium, aqueous lipid medium, aqueous vitamin medium or any combination thereof.

9. A composition of claim 1 wherein the organic solvent is selected from the group consisting of esters of carbonic acid and alkyl alcohols, alkyl esters of mono-, di-, and tricarboxylic acids, and alkyl ketones.

10. A composition of claim 1 wherein the organic solvent is selected from the group consisting of propylene carbonate, diethyl malonate, ethylene carbonate, dimethyl carbonate, 2-ethoxy ethyl acetate, ethyl acetate, methyl acetate, ethyl butyrate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate, methyl ethyl ketone.

11. A composition of claim 1 wherein the aqueous medium includes a component selected from the group consisting of an emulsifying agent, a surfactant, an excipient, a colorant and any combination thereof.

* * * * *

UNITED STATES PATENT AND TRADEMARK OFFICE
CERTIFICATE OF CORRECTION

PATENT NO. : 7,128,927 B1
APPLICATION NO. : 09/060047
DATED : October 31, 2006
INVENTOR(S) : Dunn It is certified that error appears in the above-identified patent and that said Letters Patent is hereby corrected as shown below:

On page 2, in field (56), under "Other Publications", in column 2, line 1, delete "12" and insert -- 12th --, therefor.

In column 5, line 33, delete "water body," and insert -- water, body --, therefor.

In column 6, line 3, delete "Does" and insert -- does --, therefor.

In column 6, line 4, delete "Being" and insert -- being --, therefor.

In column 7, line 23, delete "monglycerides" and insert -- monoglycerides --, therefor.

In column 8, lines 49-50, delete "2-ethyoxyethyl" and insert -- 2-ethoxyethyl --, therefor.

In column 8, line 51, delete "glutonate" and insert -- glutarate --, therefor

In column 8, line 60, delete "biocompatitibility" and insert -- biocompatibility --, therefor.

In column 8, line 66, delete "N-methylpyrrolidone" and insert -- N-methyl pyrrolidone --, therefor.

In column 9, line 1, delete "N-methylpyrrolidone" and insert -- N-methyl pyrrolidone --, therefor.

In column 9, line 3, delete "N-methylpyrrolidone" and insert -- N-methyl pyrrolidone --, therefor.

In column 10, line 9, after "enables the" delete "a".

In column 11, line 45, delete "N-methyl-2-pyrolidone" and insert -- N-methyl-2-pyrrolidone --, therefor.

In column 14, line 11, in Claim 4, after "ketal" insert -- , --.

UNITED STATES PATENT AND TRADEMARK OFFICE
CERTIFICATE OF CORRECTION

PATENT NO. : 7,128,927 B1
APPLICATION NO. : 09/060047
DATED : October 31, 2006
INVENTOR(S) : Dunn It is certified that error appears in the above-identified patent and that said Letters Patent is hereby corrected as shown below:

In column 14, line 41, in Claim 10, delete "glutonate" and insert -- glutarate --, therefor.

Signed and Sealed this

Third Day of April, 2007

JON W. DUDAS
*Director of the United States Patent and Trademark Office*